United States Patent [19]

Souda

[11] Patent Number: 4,759,685
[45] Date of Patent: Jul. 26, 1988

[54] VEHICLE FOR AERIAL WORKING

[75] Inventor: Takeshi Souda, Setagaya, Japan

[73] Assignee: Toyota Jidosha Kabushiki Kaisha, Japan

[21] Appl. No.: 867,442

[22] Filed: May 28, 1986

[30] Foreign Application Priority Data

May 30, 1985 [JP] Japan .................................. 60-81682
May 30, 1985 [JP] Japan .................................. 60-81683
Jun. 5, 1985 [JP] Japan .................................. 60-84899

[51] Int. Cl.⁴ .......................................... B66C 23/00
[52] U.S. Cl. .................................... 414/680; 414/718;
414/719; 280/755; 182/2; 212/184; 180/321
[58] Field of Search .......................... 212/189, 184;
280/755 X, 767; 414/74 YR, 687, 718 X, 719 X,
695.7, 680, 688; 182/2 X; 901/48; 180/321

[56] References Cited

U.S. PATENT DOCUMENTS

| | | | |
|---|---|---|---|
| 2,450,152 | 9/1948 | Miller | 182/2 X |
| 2,472,944 | 6/1949 | Furer et al. | 182/2 X |
| 2,627,560 | 2/1953 | Eitel | 182/2 X |
| 2,646,182 | 7/1953 | Maas | 182/2 X |
| 2,750,204 | 6/1956 | Ohrmann | 212/189 X |
| 2,973,112 | 2/1961 | Young | 182/2 X |
| 2,973,209 | 2/1961 | Shaw | 280/755 |
| 2,977,769 | 4/1961 | Troche | 182/2 X |
| 2,988,163 | 6/1961 | Foley | 182/2 |
| 3,127,952 | 4/1964 | Baerg | 182/2 |
| 3,266,636 | 8/1966 | Dorn | 414/719 X |
| 3,329,290 | 7/1967 | Lowery | 182/2 X |
| 3,841,436 | 10/1974 | Grove | 182/2 |
| 3,900,119 | 8/1975 | Olsen | 280/767 X |
| 4,241,803 | 12/1980 | Lauber | 212/189 X |
| 4,258,825 | 3/1981 | Collins | 180/321 X |
| 4,274,795 | 6/1981 | Taylor | 212/189 X |
| 4,427,121 | 1/1984 | Clements | 212/189 X |
| 4,492,511 | 1/1985 | Bilsing | 414/718 X |

FOREIGN PATENT DOCUMENTS 1030768 5/1958 Fed. Rep. of Germany.
1217450 12/1970 United Kingdom .................. 212/184

Primary Examiner—Robert J. Spar
Assistant Examiner—Jennifer Doyle
Attorney, Agent, or Firm—Parkhurst & Oliff

[57] ABSTRACT

A vehicle for aerial working includes a vehicle, a rotary base disposed at a rear portion rearwardly of a frame of the vehicle, a folding arm assembly on the rotary base for vertically extending its arm, a boom assembly having an axially extendable first jib supporting at its distal end an aerial platform, a front axle disposed at a front portion of the frame, and a rear axle disposed at the rear portion and rearwardly of the rotary base, the rear axle having a pair of wheels oppositely sidewardly projecting beyond a pair of wheels of the front axle. The boom assembly also has a second jib disposed in parallel with the first jib and supporting at its distal end a counterweight to balance with the weight of the aerial platform, wherein the second jib axially slides to move toward and away from the first jib to an extent same as the latter moves. The vehicle also includes a discrete load cart connected to the rear end of the frame, the cart supporting thereon a box-shaped pallet, and a tubular bellow chute expansibly extending between the box-shaped pallet and the platform.

10 Claims, 2 Drawing Sheets

VEHICLE FOR AERIAL WORKING

BACKGROUND OF THE INVENTION

1. Field of the Invention

The present invention relates to a vehicle for aerial working for supporting an aerial platform, and more particularly a vehicle, having a lift mechanism for supporting an aerial platform in a vertically and sidewardly movable fashion, which is suited especially for work on soft ground such as an orchard field.

2. Description of the Prior Art

A known vehicle for aerial working includes an extendable arm rotatably supported by a base on a chassis of the vehicle, and an aerial platform supported on a distal end of the arm, in which the arm is extended or folded and/or rotated under the control of an operator on the platform so as to locate the platform at a desired point in the air.

The vehicle of this type has a drawback in that as the arm is raised to increase its height, the equilibrium of the machine body tends to become unstable, particularly in a transverse direction thereof. Therefore, such conventional vehicle needs to have at least one pair of outriggers disposed outwardly of opposite sides thereof and each having a presser foot at its distal end. The presser foot is adapted to firmly engage the ground surface so as to support the vehicle firmly to thereby establish a stable equilibrium in the transverse direction of the vehicle.

When such prior vehicle is operated on soft ground e.g. an orchard field for picking fruits off tall trees, it becomes disadvantageous in that the presser foot of the outrigger at one side of the vehicle is likely to sink into the ground or otherwise to damage a root of the tree appearing near the ground surface.

The outrigger itself disadvantageously weighs much due to its heavy mechanism such as a hydraulic power unit, thus resulting in that the machine having the outriggers becomes as a whole too heavy to operate on such soft ground as the orchard field.

SUMMARY OF THE INVENTION

It is therefore an object of the present invention to provide a vehicle for aerial working, for supporting an aerial platform, which is suited for work on soft ground such as an orchard field.

Another object of the invention is to provide a light weight vehicle for supporting an aerial platform which maintains a stable equilibrium thereof during its operation without the support given by the outrigger.

According to the present invention, a vehicle for aerial working is composed of a chassis extending in the longitudinal direction of the vehicle and having a pair of front wheels on both sides of a front portion thereof and a pair of rear wheels on both sides of a rear portion thereof, a lift mechanism disposed on the chassis and having a vertically expansible unit and a platform vertically movably supported on the lift mechanism. The lift mechanism includes a rotary base disposed on the chassis and is angularly rotatable in a horizontal plane. The rear wheels are disposed rearwardly of the rotary base. The rotary base is angularly rotated within an angle defined by and between a pair of lines extending from respective centers of the rear wheels to a rotation axis of the base.

With such an arrangement, the present vehicle moves or travels lightly and smoothly even on soft ground without causing its rear wheels to sink into the ground or damage a root of a tree near the ground surface, since the vehicle has a relatively light weight due to the absence of the outriggers which have been replaced by an ordinary tire wheel assembly. The vehicle maintains its stable equilibrium in its transverse direction when it extends its arm of the lift mechanism high in the air. The vehicle is thus useful when it moves around with the arm extended high in the air.

Many other advantages, features and additional objects of the present invention will become manifest to those versed in the art upon making reference to the detailed description and the accompanying drawings in which a preferred embodiment incorporating the principles of the present invention is shown by way of illustrative example.

DETAILED DESCRIPTION

Figure 1:
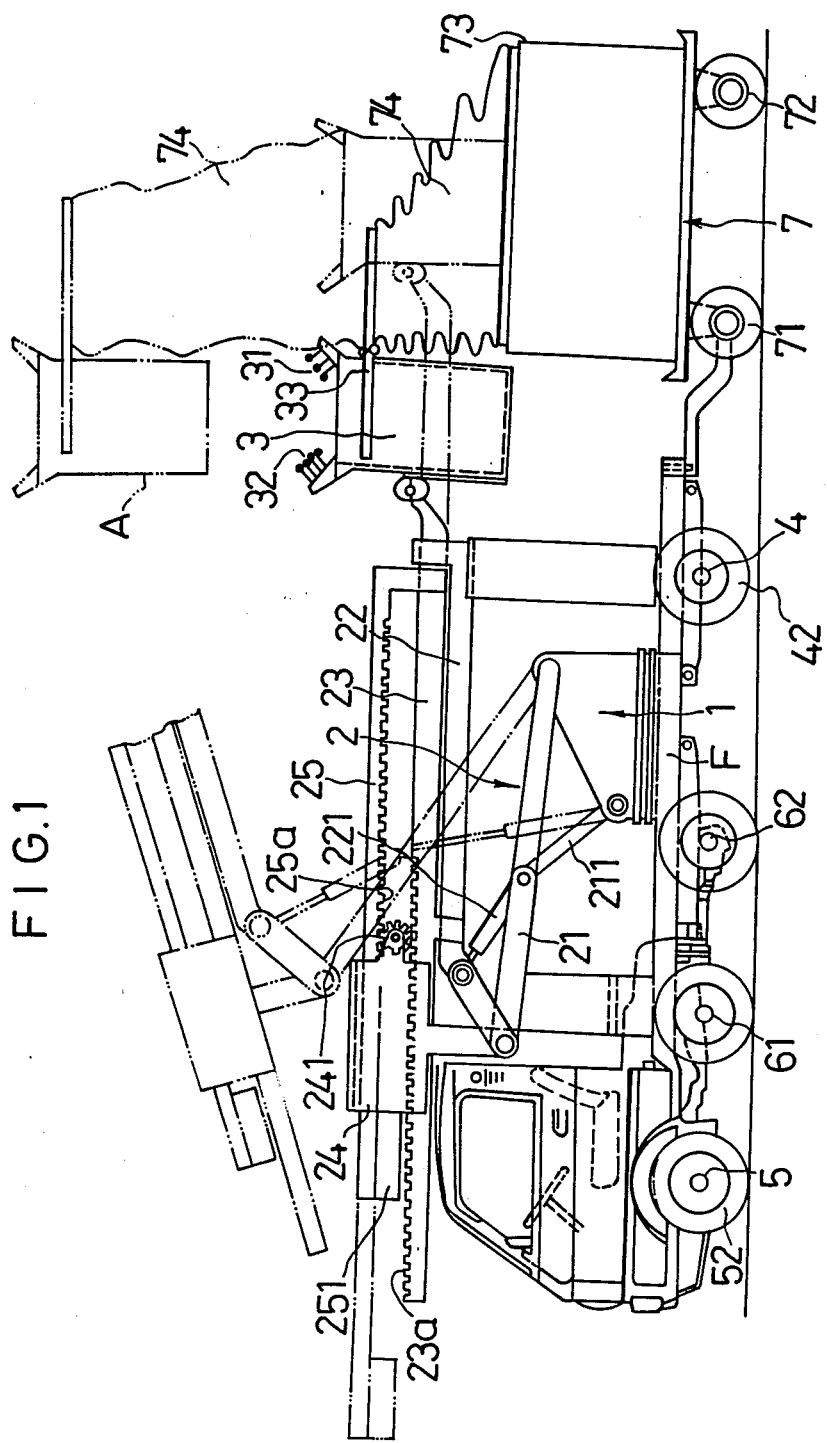
FIG. 1 is a side elevational view of a vehicle.

As shown in FIG. 1, the present vehicle for aerial working includes a vehicle having a chassis or frame F, rotary base 1 supported on the frame F at a rear portion thereof for angularly moving within an angle $\theta$ (FIG. 2) in horizontal plane, and a lift mechanism 2 supported on the rotary base 1 so as to angularly rotate upon the angular movement of the base 1.

The lift mechanism 2 includes a folding arm assembly pivotally supported on the rotary base 1, a sliding boom assembly supported on the folding arm assembly, and a drive unit having a pair of actuator cylinders 211, 221 for actuating the arm assembly. The folding arm assembly has a first arm 21 and a second arm 22 pivotally connected to each other via a joint at respective one ends. The first arm 21 is pivotally mounted at the other end to the rotary base 1, while the second arm 22 supports the boom assembly therealong. The actuator cylinder 211 is pivotally movably mounted on the rotary base 1 and has a piston rod operatively connected to the first arm 21, while the actuator cylinder 221 is mounted on the first arm 21 and has a piston rod operatively connected to the second arm 22, as shown in FIG. 1.

Upon actuation of the two actuator cylinders 211, 221, the arm assembly is extended from a folded position illustrated by a solid line to an extended position illustrated by a phantom line, with the result that the boom assembly is raised accordingly from a lower position in a solid line to an upper position in a phantom line.

The boom assembly includes a first jib 23 slidably held by the second arm 22, a second jib 25 extending over and in parallel with the first jib 23, and a support casing 24 having a lower end portion pivotally connected to the one end of the first arm 21. The first jib 23 and the second arm 22 have guides disposed thereon, respectively, axially remotely from each other in an axial direction of the jib or the arm so that the first jib and the second arm are guided slidably by each other.

The two jibs 23, 25 are slidably supported by and through the support casing 24. The second jib has a guide at its rear end for slidably guiding the first jib 23. The two jibs 23, 25 have a pair of racks 23a, 25a disposed at respective inner sides in confronting relation. The support casing has a drive pinion 241 disposed between the two racks 23a, 25a for intermeshing with the latter. A box 3 serving as a platform is mounted on a rear end of the first jib 23, while a counterweight 251 is mounted on a front end of the second jib 25, the counterweight 251 serving to balance the boom assembly against the weight of the box 3.

Figure 2:
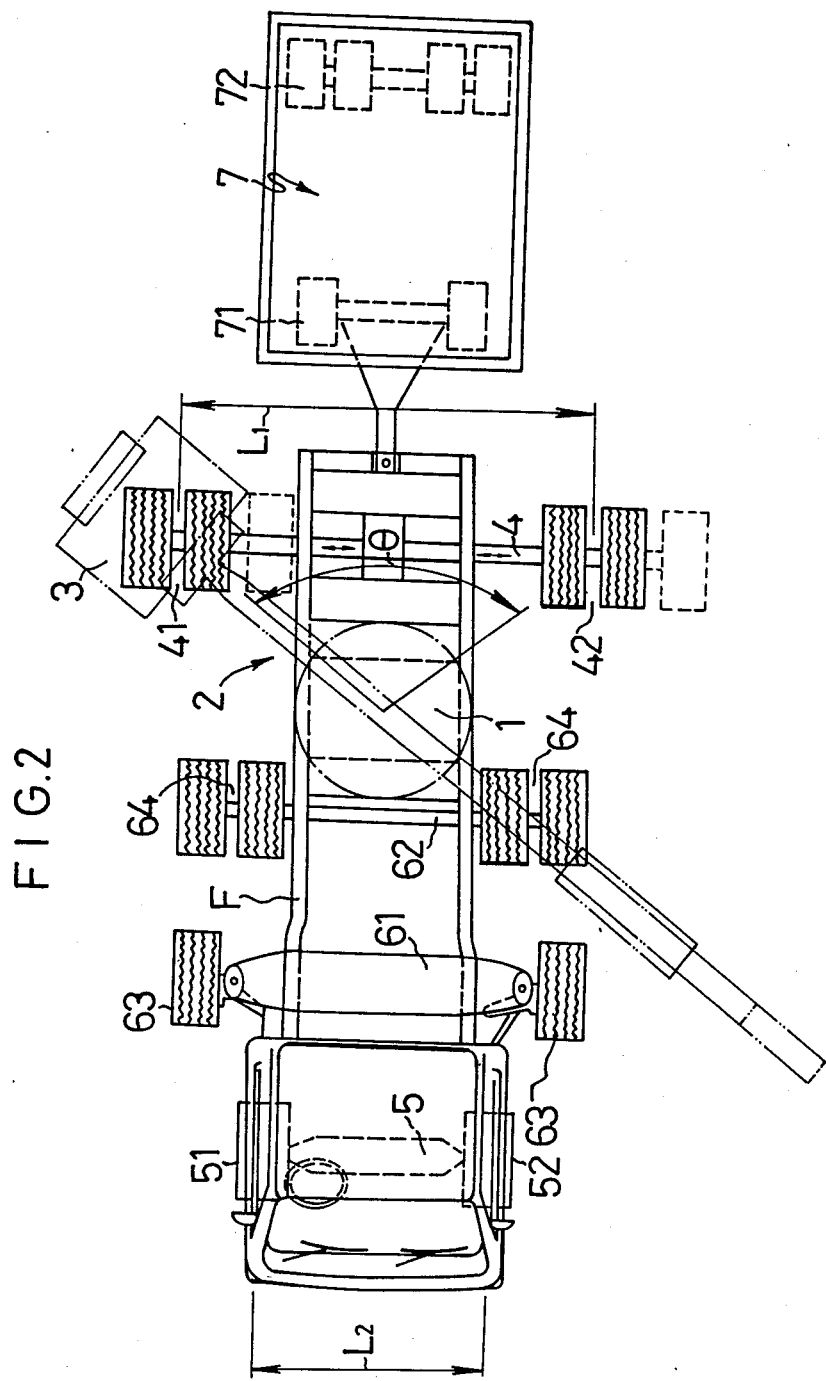
FIG. 2 is a plan view of the vehicle with certain parts omitted and a boom assembly of a lift mechanism angularly rotated to one side position.

With this arrangement, the two jibs 23, 25 can be axially moved toward and away from each other by rotatably driving the drive pinion 241 such that the two jibs move an equal distance in opposite directions to a position an example of which is shown by the phantom line in FIG. 1. As a result the counterweight 251 continues to balance the weight of the box 3 irrespective of the relative position of the two jibs, so that the loading equilibrium of the machine in a transverse direction thereof is maintained. Consequently, the moment of a rolling force on the machine is substantially eliminated even when the lift mechanism is rotated together with the boom assembly to move the box 3 to a sideward raised position as shown in FIG. 2.

The frame F is supported on a combination of a front axle 5 disposed below a cab of the vehicle, a rear axle 4 disposed rearwardly of the rotary base 1, and a pair of intermediate axles 61, 62. The axles 4, 5; 61, 62 have at their opposite ends pairs of wheels 41, 42; 51, 52; 63, 64, respectively, which consist of low pressure tires each having a contact surface of a relatively large area. The rear axle 4 extends axially outwardly longer than the other axles, so that the opposite pairs of wheels 41, 42 are outwardly protruding beyond the other pairs of the wheels on the other axles. In other words, a tread or distance L1 between the wheels 41, 42 is greater than a tread L2 of the wheels 51, 52 such that the maximum angle $\theta$ of the angular movement of the rotary base 1 is substantially equal to an angle defined by and between a pair of lines extending respectively from the centers of the wheels 41, 42 toward the rotation center of the rotary base 1, as shown in FIG. 2. With this arrangement of the wheels 41, 42, a transversely biased load which will occur, if any, on the machine especially when the box 3 is positioned to either side of the vehicle will be firmly born upon by the wheels 41, 42 on the ground, resulting in a stable load equilibrium of the vehicle in the transverse direction. Such a transversely biased load is kept at a minimum value by the vehicle according to the present invention.

The front and intermediate axles 5, 61 serve as steering axles, while another intermediate axle 64 serves as a drive axle. Accordingly, the wheels 51, 52; 63, 64 are always in contact with ground. The wheels 41, 42 serve as auxiliary support wheels which work only when such an ill-balanced load occurs as described hereinabove. To this end the wheels 41, 42 are held apart from ground in an inoperative condition thereof. With the wheels held apart from ground, the vehicle can avoid undergoing a frictional force resisting to the turning of the vehicle, the frictional force being caused by the wheel 41 or 42 during the turning. To this end, if the rear axle 4 has a suspension mechanism, the rear axle 4 may be constructed such that the same is slidable in an axial direction. Thus the axle 4 will slide axially outwardly when the vehicle turns, and thereafter it will return to an initial position when the vehicle travels straight forwardly once again.

To attain a highly maneuverable vehicle, the box 3 carries a first control panel 31 for controlling the lift mechanism 2 and a second control panel 32 for driving the vehicle remotely from the cab.

A cart 7 is connected to a rear end of the frame F, such that the vehicle tows the cart 7. The cart 7 includes a frame having a pair of wheel assemblies 71, 72 disposed thereunder. A pallet 73 of a box is supported on the base. A bellow chute 74 extends between an upper open end of the pallet 73 and a hanger rail 33 disposed on and around the box 3. The chute has an upper open end slidably supported by the hanger rail 33 and a lower open end detachably connected to the upper open end of the pallet 73. The bellow chute 74 is longitudinally expansible in response to the movement of the box 3. In FIG. 1, the bellow chute 74 upwardly extends as shown by a phantom line when the box is raised to a position A.

In operation for picking fruits off the trees, the arm assembly composed of arms 21, 22 is extended to raise the boom assembly while the latter longitudinally extends the first jib 23 in one direction so as to move the box 3 to a desired level. As the first jib 23 is extended, the second jib 25 is simultaneously extended in the opposite direction to a given extent same as the first jib to keep the load balance of the vehicle, with the result that the transversely biasing force acting on the vehicle can be decreased if any. If the transversely biasing force is created by the extension of the boom assembly, such force will only cause either of the sidewardly projected rear wheels 41, 42 to press against ground, with the result that the vehicle will be kept free from rolling or sidewardly inclining and maintain its stable equilibrium. The wheels 41, 42 each having a low pressure tire of a relatively large contact area are neither likely to sink in soft ground nor to damage roots of the trees near ground surface.

The vehicle for an aerial working according to the present invention is highly mobile in that the sidewardly projecting wheels 41, 42 enable the vehicle to maintain continuously the load equilibrium when the vehicle travels with the boom assembly raised and sidewardly rotated.

In the present vehicle, the collected friuts are loaded via bellow chute 74 onto the pallet 73 on the discrete cart 7, thus avoiding occurrence of any biasing force or impact due to the acquired load, e.g. fruits, except for the biasing force proper to the system of the present vehicle. The pallet 73 is easily replaced by a new pallet by detaching the chute 74 therefrom.

The vehicle according to the above-described embodiment of the invention includes intermediate axles 61, 62 to increase the number of wheels of the machine. The increased number of wheels achieves wide distribution of weight or load of the machine which results in a decreased air pressure of the wheel tires suited for work on soft ground. However, the intermediate axles 61, 62 may be omitted in case a larger air pressure of the wheel tires is permitted. In absence of the intermediate axles, the rear axle may serve as a drive axle.

Alternatively, such low pressure tires of the vehicle may be replaced by ordinary tires of a common pressure depending on various conditions.

The boom assembly may be modified such that the first and second jibs are driven by a drive endless wire or chain instead of the drive pinion 241.

In another embodiment of the invention, in which only a neglectably small biasing force occurs during the operation of the lift mechanism. in particular, of the boom assembly, the second jib 25 and hence the counterweight 251 may be omitted.

In still another embodiment, the intermediate axle 62 may be disposed on the rear side of the rotary base 1.

According to the present invention, a vehicle for aerial working for supporting an aerial platform maintains continuously its structual load equilibrium irrespective of whether it is in a stationary or travelling condition with no neccesity of an outrigger assembly which has been essential to the conventional machine. The present machine can travel with the platform held in a raised position. Therefore it is highly suitable for work on soft ground such as an orchard field in picking the fruits off the tall trees.

In the above-described embodiment, the counterweight is provided to restrain the occurrence of an ill-balanced load of a vehicle. Therefore, the angular movement of the rotary base may exceed the above-described maximum angle $\theta$ to a certain extent.

In the case that such a large angle $\theta$ is not required, the wheels 41, 42 need not be protruded outside the vehicle largely as compared with the other wheels 51, 52.

What is claimed is:

1. A vehicle for aerial working comprising:
   a chassis extending in the longitudinal direction of the vehicle and having a pair of front wheels on both sides of a front portion thereof and a pair of rear wheels on both sides of a rear portion thereof;
   a lift mechanism disposed on said chassis and having a vertically expansible unit;
   a platform vertically movable relative to said lift mechanism;
   said lift mechanism including a rotary base disposed on said chassis and being angularly rotatable in a horizontal plane;
   a folding arm assembly supported on said rotary base and having arms, each of said arms being driven to move from a folded position to an extended position;
   a boom assembly including a first jib supported by said arm assembly and being axially movable for supporting at its rear end said platform;
   a second jib being axially movable along said first jib for supporting at its front end a counterweight balancing with the weight of said platform;
   a drive mechanism for moving said first and second jibs in opposite axial directions to a common extend equal to each other;
   said rear wheels being disposed rearwardly of said rotary base; and
   said rotary base being angularly rotated only within an angle defined by and between a pair of lines extending from respective centers of said rear wheels to a rotation axis of said base.

2. A vehicle according to claim 1, said rear wheels protruding largely outside said chassis.

3. A vehicle according to claim 1, further including at least one pair of intermediate wheels, said at least one pair of intermediate wheels being disposed in one of the space between said front wheels and said rear wheels and the space rearward of said rear wheels, one of said at least one pair of intermediate wheels serving as drive wheels, said rear wheels being normally held out of contact with ground.

4. A vehicle according to claim 1, a rear axle provided with said rear wheels on both ends being axially slidable when the vehicle turns.

5. A vehicle according to claim 1, said front and rear wheels, respectively, being low pressure tires each having an increased contact area.

6. A vehicle according to claim 1, said first and second jibs having respective racks disposed in their respective inside walls in a confronting relation, said drive mechanism including a pinion gear disposed between said racks in an intermeshing relation to each other.

7. A vehicle according to claim 1, further including a discrete load cart including a base in the form of plate having a plurality of wheels disposed thereunder, said cart supporting a box-shaped pallet on said base and being connected to a rear end of said frame of the vehicle.

8. A vehicle according to claim 7, said platform supporting an expansible tubular chute thereon, said chute having an upper open end fixedly attached to said platform and a lower open end detachably attached to an open end of said box-shaped pallet.

9. A vehicle according to claim 1, said platform carrying thereon a control unit for controlling the vehicle and another control unit for controlling said lift mechanism.

10. A vehicle for an aerial working comprising:
    a chassis extending in the longitudinal direction of the vehicle and having a pair of front wheels on both sides of a front portion thereof and a pair of rear wheels on both sides of a rear portion thereof;
    a lift mechanism disposed on said chassis and having a vertically expansible unit;
    a platform vertically movable relative to said lift mechanism;
    said lift mechanism including a rotary base disposed on said chassis and being angularly rotatable in a horizontal plane;
    said lift mechanism further including a folding arm assembly supported on said rotary base and having arms driven to move from a folded position to an extended position and a boom assembly including a first jib supported by said arm assembly and being axially movable and supporting at its rear end said platform, a second jib being axially movable along said first jib and supporting at its front end a counterweight balancing the weight of said platform, and a drive mechanism for moving said first and second jibs to an equal extent in opposite axial directions.

* * * * *